United States Patent [19]

Smith, Jr. et al.

[11] 4,367,042

[45] Jan. 4, 1983

[54] SPECTROANALYTICAL SYSTEM

[75] Inventors: Stanley B. Smith, Jr., Westford; Carl Shapiro, West Roxbury, both of Mass.

[73] Assignee: Instrumentation Laboratory Inc., Lexington, Mass.

[21] Appl. No.: 215,674

[22] Filed: Dec. 12, 1980

[51] Int. Cl.³ ............................................. G01N 21/72
[52] U.S. Cl. .................................. 356/315; 356/417; 431/126; 431/346
[58] Field of Search ................ 356/315, 417; 431/126, 431/346

[56] References Cited

U.S. PATENT DOCUMENTS 3,525,476  8/1970  Boling et al. ......................... 239/338
3,583,844  6/1971  Smith .................................... 431/79

*Primary Examiner*—Vincent P. McGraw

[57] ABSTRACT

A spectroanalytical instrument includes burner structure and a nebulizer for furnishing sample in fog form for flow through a premix chamber to the burner structure. Flow structure extending from a chamber port to a drain port provides a condensate flow path from the chamber to a drain. Trap structure is disposed in series in the flow path between the chamber port and the drain port, and drain line closure apparatus is switched between a first condition in which the drain line is closed and a second condition in which the drain line is opened by a control responsive to liquid in the trap structure such that the drain line is initially closed and is opened automatically in response to accumulation of condensate liquid in the trap structure to enable maintenance of positive pressure in the premix chamber.

10 Claims, 5 Drawing Figures

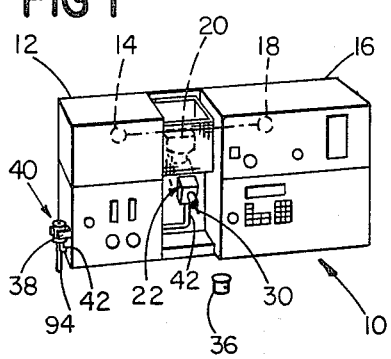
FIG 1
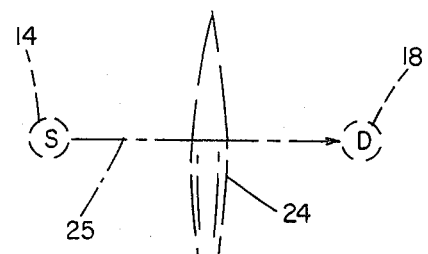
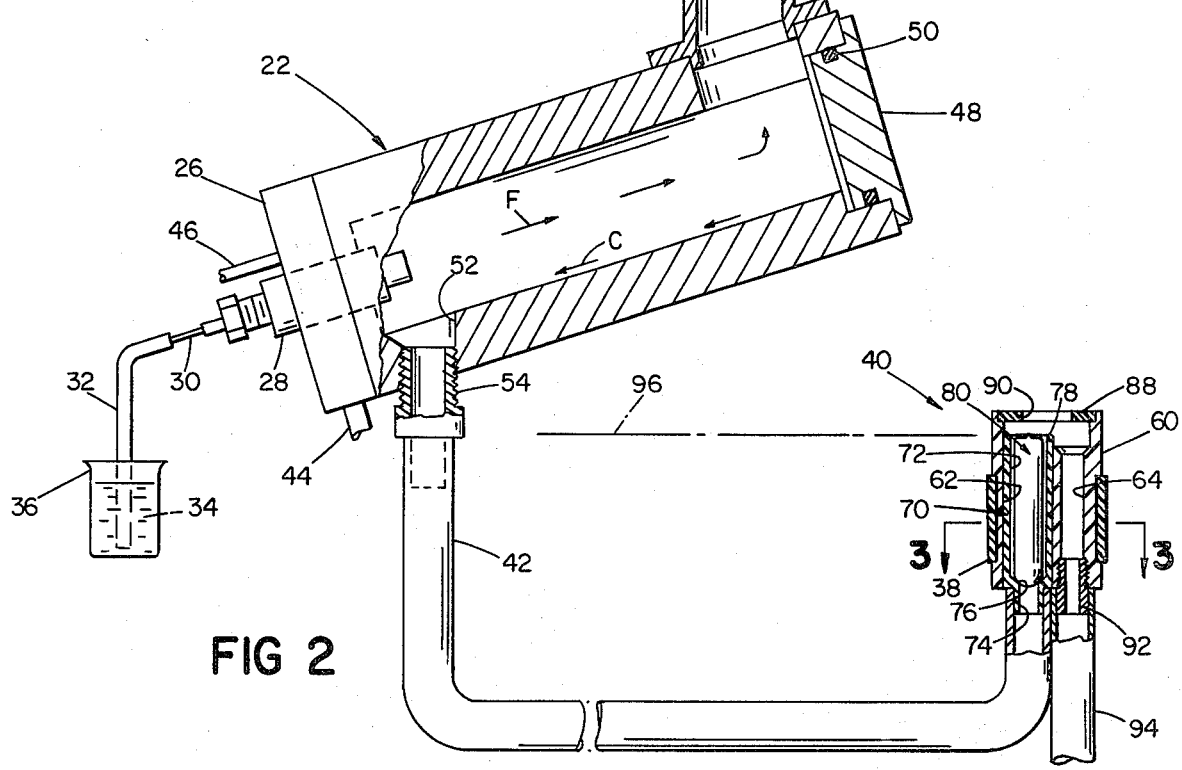
FIG 2
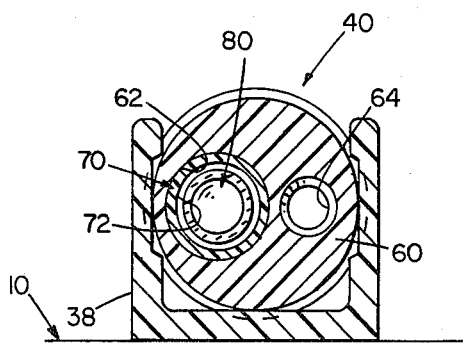
FIG 3
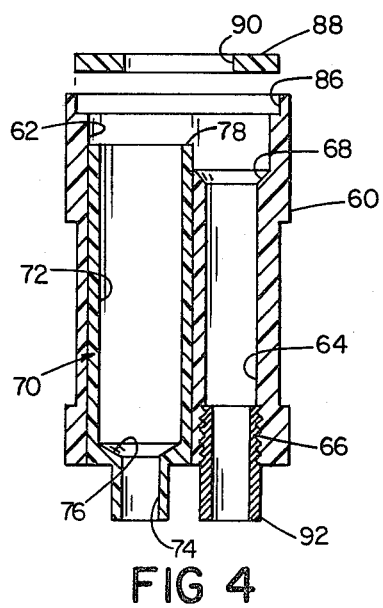
FIG 4
FIG 5

SPECTROANALYTICAL SYSTEM

This invention relates to spectroanalytical systems, and more particularly to spectroanalytical systems of the type that sense a spectral characteristic of a flame, for example, by absorption or emission technology.

In an atomic absorption type of spectroanalytical system, the material to be analyzed is introduced into a premix chamber by a nebulizer arrangement using a regulated air or oxidant stream, as a fine uniform spray of minute droplets, which droplets are entrained with a combustible fuel and flowed through the premix chamber into a burner area for combustion and production of a flame which energizes the material to be analyzed for analysis purposes. A positive pressure should be maintained within the premix chamber so that burning occurs outside the burner head, the positive pressure being sufficient to insure that the exit velocity of the fuel-sample mixture from the burner exceeds the flame propagation velocity so that flame will not propagate back through the burner into the premix chamber and create an explosion within the premix chamber. In such systems, substantial amounts of liquid condense within the premix chamber and must be removed from the chamber (typically through a chamber drain port of area comparable to that of the burner slot(s)) without detriment to the fuel-sample fog flow through the premix chamber. Trap structures have been provided in such drain lines, but if those traps are not filled with liquid, explosive "flashback" into the premix chamber occurs. Because of this risk, premix chambers are frequently formed with a frangible diaphragm or releasable cap which releases on build-up of explosive pressure so that damage to the spectral analytical apparatus is minimized. Protective systems have also been proposed which include ignition interlock arrangements for precluding ignition unless liquid is sensed in the drain trap.

In accordance with the invention, there is provided a spectroanalytical instrument that includes burner structure, and a nebulizer for furnishing sample in fog form for flow through a premix chamber to the burner structure. Flow structure extends from a chamber port to a drain port for providing a flow path for condensate from the chamber to a drain, and trap structure is disposed in series in the flow path between the chamber port and the drain port. Closure apparatus is switched between a first condition in which the drain line is closed and a second condition in which the drain line is opened by control means responsive to liquid in the trap structure such that automatically the drain line is initially closed and is opened in response to accumulation of condensate liquid in the trap structure such that positive pressure is maintained in the premix chamber whether or not the drain trap is filled with liquid.

Preferably the closure apparatus includes annular seat structure in a drain line, a cooperating closure element which in its first condition is in sealing engagement with the seat structure and in its second condition is spaced from the seat structure, and a buoyant member that is responsive to liquid level in the trap structure that moves the closure element to its second condition to allow flow of liquid through the trap structure to an overflow port, the overflow port being supported at least about one centimeter below the chamber drain port.

In a particular embodiment the trap structure includes a vertically extending cylindrical cavity of plastics material with a conical valve seat surrounding an inlet port at the lower end of the cavity, and the buoyant member is an elongated, generally cylindrical hollow glass member of smaller diameter than the cylindrical cavity, the closure element being a rounded end surface of the glass member that engages the seat. Preferably the specific gravity of the glass member is less than 0.7. The pressure control system works with a range of condensate liquids including alcohol and maintains positive premix chamber pressure in a simple, economical, and reliable manner without need for complex interlock mechanisms.

Other features and advantages of the invention will be seen as the following description of a particular embodiment progresses, in conjunction with the drawing, in which:

FIG. 1 is a perspective view of an atomic absorption instrument in accordance with the invention;

FIG. 2 is a diagrammatic sectional view of the system for maintaining pressure in the premix chamber of the instrument shown in FIG. 1;

FIG. 3 is a sectional view taken along the line 3—3 of FIG. 2;

FIG. 4 is a sectional view of components of the chamber pressure maintaining assembly; and FIG. 5 is an elevational view of the float structure employed in the system shown in FIG. 2.

DESCRIPTION OF PARTICULAR EMBODIMENT

The atomic absorption spectroanalysis instrument shown in FIG. 1 has a housing 10 with a first compartment 12 in which a radiation source 14 is disposed and a second compartment 16 in which a radiation detector 18 is disposed. Disposed between compartments 12 and 16 is burner head structure 20 that is mounted on premix chamber structure 22 and that generates a flame 24, a spectral characteristic of which is sensed by detector 18. The configuration of the burner head is a function of the fuel employed, for example a particular burner head for use with air as an oxidant employs exit orifice structure with one or more slots that are about ten centimeters in length; while a burner head for use with nitrous oxide has a single slot about seven centimeters in length. At the end of premix chamber 22 remote from burner head 20 is an end cap 26 which supports a nebulizer structure 28 that includes capillary 30. Tube 32 is connected to capillary 30 and its other end is disposed in liquid sample 34 held in container 36. Mounted on housing 10 by means of support 38 is control structure 40 that is connected to chamber 22 by means of drain tube 42.

Further details of the chamber pressure control system may be seen with reference to FIG. 2. Coupled to nebulizer structure 28 is an oxidant inlet conduit 44 and a fuel inlet conduit 46. In a particular system, air at a pressure of 40 psig is supplied through inlet 44 to nebulizer 28 to aspirate a sample from container 36 through capillary 30. A fuel-air mixture of acetylene at a pressure in the order of 6-8 psig and air at a pressure of five psig is supplied through tube 46 to produce a flow interaction such that nebulizer 28 converts the fluid sample to a fog of minute droplets which flows in a stream through premix chamber 22 (as indicated generally by arrows F) to burner head 20. The oxygen-fuel mixture droplets with entrained sample flowing from the burner head are ignited by a suitable ignition system, producing flame 24 which modifies radiation in beam 25 for sensing by detector 18. An end cap 48 at the end of chamber 22 remote from end cap 26 is frictionally secured by O-ring 50 such that it will be released on build-up of pressure in chamber 22 should the flame 24 propagate rearwardly ("flashback") through burner head 20 into chamber 22.

Drain port 52 in chamber 22 adjacent end cap 26 is connected by means of fitting 54 to drain line 42. Drain line 42, of about one centimeter internal diameter and about 50 centimeters in length, is connected to chamber pressure control assembly 40. Assembly 40 includes housing member 60 of molded plastic material (e.g., polypropylene) that has a diameter of about four centimeters and a length of about six centimeters. Formed in housing 60, as indicated in FIGS. 3 and 4, are two cylindrical through passages 62, 64, passage 62 having a diameter of about 1.7 centimeters, and passage 64 having a central section of about 0.9 centimeters diameter with a lower threaded portion 66 and an upper counter bore 68. Disposed in bore 62 is a chamber insert 70 that has a cylindrical wall 72 of about 1.4 centimeters internal diameter, an overall length of about six centimeters, a stub portion 74 that defines a passage of about 0.6 centimeter diameter, a conical valve seat 76, and an upper edge 78. Disposed within cavity 72 is a hollow float 80 (FIG. 5) of Pyrex glass that has a spherical end surface 82 and a cylindrical wall 84 and has an overall length of about five centimeters, a diameter of about 1.2 centimeters, a specific gravity of about 0.5 and a weight of about five grams. Secured on seat 86 at the upper end of housing 60 is cover disc 88 that has a port 90 of about 1.7 centimeter diameter. Tubular coupling 92 is secured to threads 66 at the base of bore 64 and drain tube 94 is connected to coupling 92. As indicated in FIG. 2, pressure control assembly 40 is supported by support 38 so that surface 78 of insert 70 is about 2.5 centimeters below the base of premix chamber 22.

At system start-up, closure portion 82 of float 80 seats on conical seat surface 76, closing drain tube 42 and allowing a positive pressure to be established in premix chamber 22. A fuel-oxidant mixture flowing through chamber 22 and burner head 20 is ignited by conventional ignition means (not shown) while condensate C from the fog of droplets flows along the lower surface of chamber 22 and into drain port 52 and drain tube 42. As the condensate fills drain tube 42, the liquid level rises in stub 74 and contacts closure surface 82 of float 80. Further accumulation of condensate in drain liner 42 eventually raises float 80, allowing condensate liquid to flow past valve seat 76 and to rise in control cavity 72. The liquid level in drain line 42 is controlled by overflow surface 78 (with excess flowing into drain line 94 to waste) so that the liquid level in drain line 42 never rises above line 96 and remains well below the bottom of premix chamber 22. Thus, at start-up, chamber drain port 52 is effectively sealed from atmosphere by the seating of closure surface 82 on seat 76 sufficient to maintain a positive pressure (typically about one inch of water) in chamber 22 and prevents flashback. When condensate accumulation in drain tube 42 is sufficient to raise float 80, the condensate in drain tube 42 acts to seal drain port 52 from atmosphere such that the desired positive pressure condition is maintained in chamber 22.

While a particular embodiment of the invention has been shown and described, various modifications thereof will be apparent to those skilled in the art. For example, it will be apparent that the invention is applicable to other types of spectroanalytical systems such as flame photometers. It is therefore not intended that the invention be limited to the disclosed embodiment or to details thereof and departures may be made therefrom within the spirit and scope of the invention.

What is claimed is:

1. In a spectroanalytical instrument comprising means defining an optical axis, a burner disposed below said optical axis for producing a flame to energize a sample to be analyzed so that said flame passes through said optical axis,
   a premix chamber connected to said burner structure, and means for furnishing sample in fog form to said premix chamber so that said sample may be aspirated for flow through said premix chamber to said burner structure,
   a pressure control system for maintaining pressure in said premix chamber so that sample fog flow velocity is in excess of the flame propagation velocity while allowing discharge of condensate from said premix chamber comprising flow path structure extending from a port in said premix chamber to a drain port to provide a condensate discharge path, trap structure in series in said condensate discharge path,
   flow path closure apparatus having a first condition in which said discharge path is closed blocking liquid flow to said drain port and a second condition in which said discharge path is open to liquid flow, and control means responsive to liquid in said trap structure for switching said closure apparatus between said first and second conditions.

2. The system of claim 1 wherein said closure apparatus includes annular seat structure in said flow structure, and a cooperating closure element which in a first condition is in sealing engagement with said seat structure to close said flow structure and in a second condition is spaced from said seat structure to open said flow structure.

3. The system of claim 1 wherein said control means includes a buoyant member that is responsive to liquid level in said trap structure for moving said closure element to said second condition.

4. The system of claim 3 wherein the specific gravity of said buoyant member is less than 0.7.

5. The system of either claim 3 or 4 wherein said buoyant member is of elongated configuration and said closure element is an end surface of said buoyant member that engages said seat.

6. The system of claim 1 wherein said trap structure has an overflow port, and further including means for supporting said overflow port at least about one centimeter below said chamber drain port.

7. The system of claim 1 wherein said trap structure includes a vertically extending cylindrical cavity of polymeric material with an inlet port at the lower end of said cavity and a conical valve seat surrounding said inlet port.

8. The system of claim 7 wherein said control means includes a buoyant member that is disposed within said cavity, said buoyant member being of elongated, generally cylindrical configuration of smaller diameter than said cylindrical cavity.

9. The system of claim 8 wherein said buoyant member has a specific gravity of less than 0.7, said cavity has an overflow port above said inlet port, and further including means supporting said overflow port at least about one centimeter below said chamber drain port.

10. The system of either claim 3 or 9 wherein said buoyant member is a hollow glass member and said closure element is a semi-spherical end surface of said glass member for seating engagement on said conical valve seat.

* * * * *